United States Patent [19]

Dworschack et al.

[11] 3,933,588

[45] Jan. 20, 1976

[54] ENZYME TREATMENT

[75] Inventors: Robert G. Dworschack, Clinton, Iowa; William H. White, Fulton, Ill.; James C. Chen, Clinton, Iowa

[73] Assignee: Standard Brands Incorporated, New York, N.Y.

[22] Filed: Aug. 23, 1974

[21] Appl. No.: 499,818

Related U.S. Application Data

[63] Continuation-in-part of Ser. No. 191,817, Oct. 22, 1971, abandoned.

[52] U.S. Cl. .................................. 195/68; 195/31 F
[51] Int. Cl.² ............................................. C07G 7/02
[58] Field of Search ....... 195/68, 63, 65, 66 R, 31 F

[56] References Cited
UNITED STATES PATENTS

| | | |
|---|---|---|
| 3,272,717 | 9/1966 | Jurchiro et al. .......................... 195/68 |
| 3,490,995 | 1/1970 | Wallenfuls et al. ................ 195/66 R |
| 3,681,197 | 8/1972 | Smith ...................................... 195/63 |
| 3,694,314 | 9/1972 | Loyd et al. .......................... 195/31 F |

OTHER PUBLICATIONS

Takasaki et al., article in Fermentation Advances, 1969, (edited by Perlman), pp. 561–569, relied on.

*Primary Examiner*—Lionel M. Shapiro

[57] ABSTRACT

Upon storage, the activity of immobilized enzymes slowly decreases in the presence of moisture. This decrease in activity can be reduced by a significant extent by treating the immobilized enzymes in the presence of moisture with a long chain quaternary ammonium compound.

9 Claims, No Drawings

ENZYME TREATMENT

THE INVENTION

This application is a continuation-in-part of patent application Ser. No. 191,817, filed Oct. 22, 1971 now abandoned.

This invention relates to a method of treating immobilized enzymes. In particular, this invention relates to a method of treating immobilized enzymes in the presence of moisture.

In the presence of moisture, immobilized enzymes have a tendency to be slowly denatured or lose activity upon storage. This tendency can be somewhat lessened by drying the immobilized enzymes but since certain enzymes are extremely heat sensitive, such drying must be performed at relatively low temperatures, thereby requiring extended drying periods. Immobilized enzymes may also be stored frozen to lessen loss of activity upon storage. These methods, however, are not entirely satisfactory from a commercial viewpoint due to the economics involved therewith and other factors.

U.S. Pat. No. 3,681,197 to Smith discloses a method for maintaining the biological activity of various soluble enzymes. In general, the method comprises providing an alcoholic solution containing a carbohydrate substrate for an amylolytic enzyme such as sorbitol, a bromine or chlorine donor such as cetyl pyridinium chloride, $NH_4Cl$ or $NH_4Br$ and carbonic anhydrase and then adding to this relatively complex solution an amylolytic enzyme. There is apparently a reaction between the constituents of the mixture which imparts a stabilizing effect to the enzyme.

U.S. Pat. No. 3,272,717 to Fukumoto et al. discloses a method of preparing a thermally stable amylase composition. In this method, an amylase is mixed with a cationic surface active agent, the mixture filtered and an organic solvent and starch added successively to the filtrate to cause a precipitate to form containing the amylase and drying the precipitate.

It is the principal object of the present invention to provide a convenient and economical method of treating immobilized enzymes in the presence of moisture to improve their storage stability.

This object and other objects which will be apparent from the following description may be obtained by treating an enzyme preparation consisting essentially of immobilized enzymes and water with an amount of a long chain quaternary ammonium compound, the amount of the compound being sufficient to increase the storage stability of said immobilized enzymes as compared to the storage stability of immobilized enzymes which have not been treated with said compound.

Exemplary of immobilized enzymes which may be treated in accordance with the present invention are glucose isomerase, alpha-amylase, α-1, 6-glucosidases, catalase, malt enzymes, glucose oxidase, cellulase and the like. The preferred immobilized enzymes which may be treated are glucose isomerase, alpha-amylase and pullulanase.

A relatively large number of long chain quaternary ammonium compounds may be used in the present method. These quaternary ammonium compounds may be represented by the following formula:

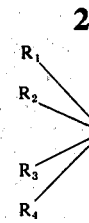

where $R_1$ is a radical containing at least 10 carbon atoms, $R_2$ is a radical containing from 1 to 20 carbon atoms and $R_3$ and $R_4$ are radicals containing not more than 6 carbon atoms, the radicals being selected from the group consisting of alkyl, substituted alkyl, alkene, aryl, substituted aryl, aralkyl, and saturated and unsaturated cyclic, wherein the cyclic radical is formed by joining $R_3$ and $R_4$, and when the cyclic radical is unsaturated, there is no $R_2$.

X may be any suitable inorganic or organic anion, such as a halide, nitrate, sulfate, acetate, etc.

Exemplary of quaternary ammonium groups represented by the above formula which may be used in the process of the present invention are trimethyloctadecylammonium, dimethylbenzyldodecylammonium, N, N-diethylmorpholynium, cetylpyridinium, trihydroxyethyloctadecylammonium, diethyldioctadecylammonium, dioctadecylmorpholynium, dimethyldilaurylammonium, and 2-chloroethylbutyldistearylammonium.

The preferred quaternary ammonium compounds used in the present method may be represented by the following formula:

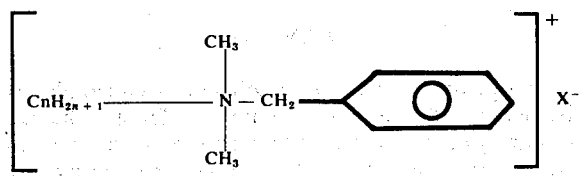

where X is a halide radical and n is an integer equal to 12, 14 or 16.

Formulations containing these compounds are sold under the trade names of Variquat 415 and Hyamine 3500 sold by Northern Petrochemical Company and Rohm and Haas Company, respectively. These formulations are a mixture composed of 50 percent of a compound where n in the above formula is 14, 40 percent of a compound where n in the above formula is 12 and 10 percent of a compound where n in the above formula is 16.

The conditions under which the immobilized enzymes are treated may vary depending upon the particular enzyme being treated and the particular long chain quaternary ammonium compound used. The amount of water present must be sufficient, of course, to dissolve the long chain quaternary ammonium compounds so that the immobilized enzymes are in intimate contact therewith.

Enzymes are produced by microorganisms intracellularly and/or extracellularly. Alpha-amylase is an example of an enzyme produced extracellularly and glucose isomerase, produced by certain microorganisms of the Streptomyces genus, is an example of an enzyme produced primarily intracellularly. Enzymes produced extracellularly are in soluble form and, if used in this form, can be recovered only by relatively costly techniques, such as ultra-filtration. Some enzymes produced intracellularly may be immobilized within the cells so that during use they are not leached or solubilized and thus may be used in a number of reactions or in continuous type systems. Enzymes may be bound or immobilized in or on inert carriers such as cellulose derivatives, e.g., DEAE cellulose, dextrans, resins, glass, and a variety of other materials. To bind or immobilize enzymes to inert carriers, it is generally necessary for the enzyme to be in soluble form. In the case of enzymes produced intracellularly, this requires the rupturing of the cell walls to free the enzymes.

The method of the present invention is applicable to immobilized enzymes whether immobilized intracellularly or immobilized in or on inert carriers.

The amount of the long chain quaternary compounds used in the present method may vary depending upon a number of factors. When the immobilized enzymes are in a relatively pure state, lesser amounts of quaternary ammonium compounds are required to obtain increased storage stability. Generally, however, in the case of immobilized glucose isomerase immobilized on or in an inert carrier, from about 0.05 to about 0.8 percent of the quaternary ammonium compounds provide satisfactory results.

In order to more clearly describe the nature of the present invention, specific examples will hereinafter be described. It should be understood, however, that this is done solely by way of example and is intended neither to delineate the scope of the invention nor limit the ambit of the appended claims.

EXAMPLE I

This Example illustrates treating intracellular glucose isomerase which has been immobilized within the cells of microorganisms of the Streptomyces genus by a heat treatment with a long chain quaternary ammonium compound.

Streptomyces sp. ATCC 21175 was cultivated in a suitable medium under aerobic conditions for a period of about 50 hours. The pH of the whole fermentor broth was adjusted with NaOH to 7.5 and the temperature adjusted to 75°C. The broth was maintained under these conditions for 5 minutes and then cooled to 40°C. A sufficient amount of Variquat 415 was added to the broth to obtain therein 0.062 percent based on the volume of the broth. The broth was filtered and the filter cake washed. The activity of the filter cake was 200 IGIU per gram. Samples of the filter cake were stored at various temperatures shown in Table I below for 27 days and the activities of the samples determined.

TABLE I

Storage Stability of Immobilized Intracellular Glucose Isomerase

| Temperature at which immobilized intracellular glucose isomerase was stored | Activity of sample dry basis (IGIU/gm)* after storage for 27 days |
|---|---|
| 40°F | 200 |
| 80°F | 200 |

*IGIU is the abbreviation of International Glucose Isomerase Units and is that amount of enzyme which will convert 1 micromole of glucose to fructose per minute in a solution containing 2 moles glucose, 0.02 moles $MgSO_4$, 0.001 moles $CoCl_2$ per liter at pH of 6.84 to 6.85 (0.2M sodium maleate) and a temperature of 60°C.

A control sample of intracellular glucose isomerase was immobilized and treated according to the general procedure described above except that no Variquat 415 was used. The sample was stored at 40°F for 27 days and the activity thereof determined. After storage, the sample had lost about 35 percent of its initial activity.

EXAMPLE II

This Example illustrates treating the glucose isomerase which has been immobilized on an inert carrier with a long chain quaternary ammonium compound.

Streptomyces sp. ATCC 21175 was cultivated in a suitable medium under aerobic conditions for a period of about 50 hours. To 7 liters of the broth were added 70 ml of 0.1 M $CoCl_2 6H_2O$, 105 gms of filter aid and 0.06 percent of cationic surfactant. The pH of the broth was adjusted to 6.5, and the temperature of the broth was maintained at 40°C. The broth was maintained under these conditions for 18 hours and then filtered. 150 gm of Whatman DE-23 Cellulose was added to the filtrate and the mixture stirred until about 100 percent of the glucose isomerase in the filtrate was adsorbed on the Whatman DE-23 Cellulose. The mixture was filtered and the filter cake washed with 1 liter of water, 1 liter of 0.1 M NaCl and 1 liter of water containing 0.05 percent Variquat 415, and the filter cake air dried to a moisture level of about 40 percent. Samples of the filter cake were then stored under the conditions described in Table II and the activities thereof determined. Other samples of immobilized glucose isomerase were prepared as described above except that no Variquat 415 was used. These samples were stored under the conditions described in Table II and the activities thereof determined.

TABLE II

Storage Stability of Glucose Isomerase Immobilized on an Inert Carrier

| Sample Treatment | Initial Activity of Immobilized Glucose Isomerase | Temperature at which Immobilized Glucose Isomerase was stored (°C) | Activity after storage (IGIU/gm dry basis) Storage Period | | |
|---|---|---|---|---|---|
| | | | 2 weeks | 1 month | 2 months |
| Variquat 415 | 446 | 5 | 446 | 446 | 446 |
| " | " | 21 | 432 | 430 | 433 |
| " | " | 37.7 | 433 | 420 | 425 |
| no Variquat 415 | 431 | 5 | 431 | 434 | 433 |
| " | " | 21 | 297 | 135 | 5 |
| " | " | 37.7 | 178 | 116 | 0 |

From the above table it is seen that at low storage temperatures, e.g. 5°C, there is little or no loss of enzyme activity whether or not the samples were treated with Variquat 415. At higher temperatures, however, the samples which were not treated lost a significantly greater proportion of their activity than the samples treated with Variquat 415.

EXAMPLE III

This Example illustrates treating pullulanase which has been immobilized on a cellulose derivative with a long chain quaternary ammonium compound.

*Aerobacter aerogenes* NRRL 289 was cultivated in a suitable medium containing maltose and dextrose under submerged aerobic conditions at 30°C for 18 hours. The medium was filtered and the filter cake containing pullulanase was washed. The filter cake was slurried in water and the pullulanase extracted by the use of a nonionic surfactant. The slurry was filtered and into the filtrate containing the pullulanase was incorporated cyanogen bromide activated cellulose. The pullulanase was immobilized through covalent bonding to the cyanogen bromide activated cellulose. Samples of the immobilized pullulanase were slurried in a 0.1 M NaCl solution, filtered, the filter cake washed with water and then with water containing 0.05 percent Variquat 415. Another sample of immobilized pullulanase was prepared in the manner described above except it was not treated with Variquat 415. The initial activities of the samples were determined and the samples were then stored for a period and the activities of the samples again determined. The results of these determinations are shown in Table III below.

TABLE III

Storage Stability of Pullulanase Covalently Bound to Cyanogen Bromide Activated Cellulose

| Sample Preparation | Initial Activity (IU*/gm) of bound pullulanase | Activity of bound pullulanase after storage for 7 days |
|---|---|---|
| Treated with Variquat 415 | 53 | 52 |
| No Variquat 415 treatment | 53 | 36 |

*One IU is defined as that amount of material which will catalyze the hydrolysis of one micromole of α-1, 6 bonds (based on release of maltotriose) per minute from a 0.5 percent pullulan solution at pH 5.0 and 45°C.

The terms and expressions which have been employed are used as terms of description and not of limitation, and it is not intended in the use of such terms and expressions to exclude any equivalents of the features shown and described or portions thereof, since it is recognized that various modifications are possible within the scope of the invention claimed.

What is claimed is:

1. A method of improving the storage stability of enzymes which are immobilized intracellularly or immobilized in or on an inert carrier comprising treating an immobilized enzyme preparation consisting essentially of immobilized enzymes and water with an amount of a compound having the following formula:

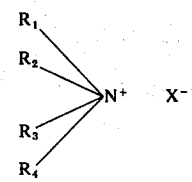

where $R_1$ is a radical containing at least 10 carbon atoms, $R_2$ is a radical containing from 1 to 20 carbon atoms, and $R_3$ and $R_4$ are radicals containing not more than 6 carbon atoms, the radicals being selected from the group consisting of alkyl, substituted alkyl, alkene, aryl, substituted aryl, aralkyl, and saturated and unsaturated cyclic wherein the cyclic radical is formed by joining $R_3$ and $R_4$, and when the cyclic radical is unsaturated, there is no $R_2$, the amount of the compound being sufficient to increase the storage stability of said immobilized enzymes as compared to the storage stability of immobilized enzymes which have not been treated with said compound.

2. A method of improving the storage stability of immobilized enzymes as defined in claim 1, wherein the immobilized enzyme is selected from the group consisting of immobilized glucose isomerase, immobilized alpha-amylase, immobilized α-1, 6-glucosidases, immobilized catalase, immobilized malt enzymes, immobilized glucose oxidase and immobilized cellulase.

3. A method of improving the storage stability of immobilized enzymes as defined in claim 2, wherein the immobilized enzymes are treated with an effective amount of a compound having the following formula:

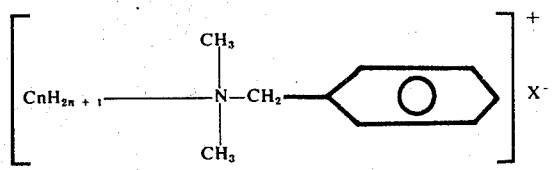

where X is a halide radical and n is an integer equal to 12, 14 or 16.

4. A method of improving the storage stability of immobilized enzymes as defined in claim 3, wherein the immobilized enzyme treated is immobilized glucose isomerase.

5. A method of improving the storage stability of immobilized enzymes as defined in claim 3, wherein the immobilized enzyme treated is immobilized alpha-amylase.

6. A method of improving the storage stability of immobilized enzymes as defined in claim 3, wherein the immobilized enzyme is immobilized pullulanase.

7. A method of improving the storage stability of immobilized enzyme as defined in claim 4, wherein the immobilized glucose isomerase being treated is immobilized on a derivative of cellulose.

8. A method of improving the storage stability of immobilized enzymes as defined in claim 3, wherein the amount of the compound used to treat the immobilized enzymes is from about 0.05 to about 0.8 percent based on the amount of moisture present.

9. A method of improving the storage stability of immobilized enzymes as defined in claim 7, wherein the derivative of cellulose is DEAE cellulose.

* * * * *

UNITED STATES PATENT OFFICE
CERTIFICATE OF CORRECTION

PATENT NO. : 3,933,588

DATED : January 20, 1976

INVENTOR(S) : Robert G. Dworschack, William H. White, James C. Chen, and Alfred A. Khwaja It is certified that error appears in the above-identified patent and that said Letters Patent are hereby corrected as shown below:

Title page, §[75]; Alfred A. Khwaja should be listed as one of the inventors.

Title page, right hand column, line 1; "Wallenfuls" should read --Wallenfels--.

Column 1, line 29: "$NH_4C/$" should read --$NH_4Cl$--.

Column 2, line 62: column 3, line 38 and line 41; column 4, line 26; "Streptomyces" should be italicized.

Column 4, line 29; "$CoCl_26H_2O$" should read --$CoCl_2 \cdot 6H_2O$--.

Signed and Sealed this

First Day of February 1977

[SEAL]

Attest:

RUTH C. MASON
Attesting Officer

C. MARSHALL DANN
Commissioner of Patents and Trademarks